US005702486A

United States Patent [19]
Craig et al.

[11] Patent Number: 5,702,486
[45] Date of Patent: Dec. 30, 1997

[54] MODULAR HUMERAL PROSTHESIS FOR RECONSTRUCTION OF THE HUMERUS

[75] Inventors: Edward Vincent Craig, Edina; Richard Frank Kyle, Long Lake, both of Minn.; Christopher Bryan Straight, Cockeysville, Md.

[73] Assignee: Kirschner Medical Corporation, Timonium, Md.

[21] Appl. No.: 626,958

[22] Filed: Apr. 3, 1996

Related U.S. Application Data

[62] Division of Ser. No. 198,036, Feb. 22, 1994, Pat. No. 5,507,817.

[51] Int. Cl.⁶ .................................................. A61F 2/36
[52] U.S. Cl. ........................................................ 623/23
[58] Field of Search ................................ 623/19, 22, 23

[56] References Cited

U.S. PATENT DOCUMENTS

| | | |
|---|---|---|
| 3,694,820 | 10/1972 | Scales et al. . |
| 3,803,641 | 4/1974 | Golyakhovsky . |
| 3,842,442 | 10/1974 | Kolbel . |
| 3,916,451 | 11/1975 | Buechel et al. . |
| 3,979,778 | 9/1976 | Stroot . |
| 4,003,095 | 1/1977 | Gristina . |
| 4,040,131 | 8/1977 | Gristina . |
| 4,042,980 | 8/1977 | Swanson et al. . |
| 4,045,825 | 9/1977 | Stroot . |
| 4,115,875 | 9/1978 | Rambert et al. . |
| 4,206,517 | 6/1980 | Pappas et al. . |
| 4,261,062 | 4/1981 | Amstutz et al. . |
| 4,355,427 | 10/1982 | Schneider . |
| 4,404,691 | 9/1983 | Buning et al. . |
| 4,550,450 | 11/1985 | Kinnett . |
| 4,693,723 | 9/1987 | Gabard . |
| 4,822,370 | 4/1989 | Schelhas . |
| 4,865,605 | 9/1989 | Dines et al. . |
| 4,878,917 | 11/1989 | Kranz et al. . |

(List continued on next page.)

FOREIGN PATENT DOCUMENTS

| | | |
|---|---|---|
| 0251583 | 1/1988 | European Pat. Off. . |
| 549480 | 6/1993 | European Pat. Off. ............... 623/22 |

OTHER PUBLICATIONS

"True/Flex™ Humerus Rod System," Applied Osteo Systems, Inc. 1991.

(List continued on next page.)

*Primary Examiner*—Michael J. Milano
*Attorney, Agent, or Firm*—Banner & Witcoff, Ltd.

[57] ABSTRACT

The invention is directed to a modular humeral prosthesis for implantation into a humerus of a patient. The prosthesis includes a proximal humeral component having a platform disposed on an upper end. A tapered projection is disposed on the platform. A cup-shaped fracture cap having a tapered opening with generally the same shape as the tapered projection is removably disposable on the tapered projection. The fracture cap is shaped so as to allow for space between the cap and the glenold of a patient into whom the prosthesis is to be implanted and thereby allow the bones of the patient's humeral head to be reconstructed by reassembling and securing the bone fragments about the fracture cap. The prosthesis further includes a humeral head having a tapered opening which may be disposed on the proximal humeral component. The humeral head is interchangeable with the fracture cap. The prosthetic humeral head may be inserted into the patient's glenoid to replace the patient's natural humeral head in fracture cases where the natural humeral head is not viable, in arthritis cases where cartilage is degenerated, or where head fracture reconstruction is attempted but fails. The fracture cap and humeral head are both modular so as to as allow caps and heads of differing sizes to be disposed on the proximal humeral component. The prosthesis also includes a modular distal stem extension which may be secured and locked on the distal end of the proximal humeral component. The distal stem extension allows the overall length of the prosthesis to be selectively increased, thereby allowing the prosthesis to be fitted to patient's having humeral shafts of differing sizes.

10 Claims, 10 Drawing Sheets

U.S. PATENT DOCUMENTS

| | | |
|---|---|---|
| 4,919,669 | 4/1990 | Lannelongue . |
| 4,919,670 | 4/1990 | Dale et al. . |
| 4,995,883 | 2/1991 | Demane et al. ............... 623/18 X |
| 5,002,578 | 3/1991 | Luman . |
| 5,002,581 | 3/1991 | Paxson et al. . |
| 5,074,879 | 12/1991 | Pappas et al. ............... 623/18 |
| 5,080,685 | 1/1992 | Bolesky et al. . |
| 5,181,928 | 1/1993 | Bolesky et al. . |
| 5,209,753 | 5/1993 | Biedermann et al. ............... 606/72 |
| 5,282,865 | 2/1994 | Dong ............... 623/19 |
| 5,314,426 | 5/1994 | Pohl et al. ............... 606/58 |
| 5,314,479 | 5/1994 | Rockwood, Jr. et al. . |
| 5,358,524 | 10/1994 | Richelsoph ............... 623/16 |
| 5,405,394 | 4/1995 | Davidson ............... 623/20 |
| 5,489,309 | 2/1996 | Lackey ............... 623/19 |

OTHER PUBLICATIONS

"Russel–Taylor® Humeral Interlocking Nail System," Smith & Nephew Richards, Inc.

Craig, Edward V., "Prosthetic Replacement for Four–Part Fractures of the Proximal Humerus," Operative Techniques in Shoulder Surgery, Ch. 27, pp. 187–196, 1991.

Burkhead, Jr., Wayne Z., "The Intermedics Select Shoulder System," Intermedics Orthopedics™, Inc. 1992.

Endotec Product Brochure, "Buechel–Pappas™ Femoral Stem System".

Endotec Product Brochure, "Buechel–Pappas™ Total Shoulder System," Implants and Instruments.

Endotec Product Brochure, "Buechel–Pappas™ Total Shoulder System," Surgical Procedure.

Biomet Product Brochure, "Bio–Modular© Total Shoulder," Biomet, Inc. 1989.

Biomet Product Brochure, "Bio–Modular© Total Shoulder," Surgical Technique, Biomet, Inc.

Biomet Product Brochure, "Uniflex™ Humeral Nail System," Biomet, Inc. 1991.

Matsen, et al., "Global™ Total Shoulder Arthroplasty System," DePuy, Inc.

Product Brochure, "The Intermedics Select® Shoulder System," Intermedics Orthopedics™, Inc.

Craig, Edward V., "Prosthetic Replacement for Four–Part Fractures of the Proximal Humerus," in *Operative Techniques in Shoulder Surgery*, Lonnie E. Paulos and James E. Tibone (eds.), Aspen Publishers, Inc., 1991.

MODULAR HUMERAL PROSTHESIS FOR RECONSTRUCTION OF THE HUMERUS

This application is a divisional of application Ser. No. 08/198,036, filed Feb. 22, 1994 now U.S. Pat. No. 5,507,817.

BACKGROUND OF THE INVENTION

1. Field of the Invention

This invention is directed to a modular humeral prosthesis which allows for total shoulder joint replacement and reconstruction of the human humerus.

2. Description of the Prior Art

Humeral prostheses are known in the art and are used for replacing the shoulder joint in humans. These prostheses generally include an elongated stem portion disposed within the humeral shaft, and a prosthetic humeral head which replaces the natural humeral head and is disposed within the shoulder socket. Currently, an accepted method of treatment for three and four-part and humeral head split fractures, in which the blood supply to the fragments is compromised, is to perform a hemiarthroplasty, replacing the humeral head with a prosthesis. Experience has shown that hemiarthroplasty affords favorable results as compared to non-operative treatments. This is because the blood supply is often compromised to the humeral head fracture pans and osteonecrosis often occurs.

U.S. Pat. No. 4,865,605 to Dines et al discloses an example of such a prior an modular shoulder prosthesis. The prosthesis includes an elongated stem portion having a planar support surface which supports a semi-spherical humeral head at one end. One of the support surface and the humeral head includes a stem, and the other includes a bore. The stem and bore are both tapered to allow the head to be disposed on the shaft with a friction fit. A similar structure is disclosed in U.S. Pat. No. 4,191,670 to Dale et al.

In both Dale et al and Dines et al, the head and stem portion are modular, that is, they are made available in different sizes but with a uniformly-sized tapered stem and bore. Accordingly, an elongated stem portion of appropriate size may be selected, and each of the different-sized heads may be removably disposed on the selected elongated stem portion while it is disposed in the humera shaft. This structure allows the surgeon to accurately balance the tension of the soft tissue about the shoulder during implantation of the prosthesis by intraoperatively evaluating different humeral head sizes. If it is necessary to make revisions to the size of the head, the revision can be made without having to remove the elongated stem portion. Though effective in total shoulder joint replacement, that is, where the humeral shaft is healthy and the prosthesis is inserted for the purpose of replacing the joint between the healthy humeral shaft and the shoulder, the devices disclosed in Dines et al and Dale et al are not ideal for treatment of humeral shaft fractures.

In contrast to the above-discussed prostheses, humeral nails or rods are designed specifically for humeral shaft fractures. Humeral nails or rods are generally cylindrical, and are inserted into the intramedullary canal of the fractured humerus. Once inserted, the nail or rod may be secured in place, for example, by cross screws extending through both the nail and the bone, or by a screw cap secured at the upper end. In order to make use of nails, both the humeral head and a portion of the humeral shaft extending at least 2-3 cm from the surgical neck of the humerus must be intact. Thus, humeral nails are of no use in treating fractures of the humeral head, or of the humeral head region.

Further, the prior art is not ideal for treating fractures of the humeral head in which it is desired to repair the fractured head. In some cases, where the blood circulation to the fracture fragments is adequate, the fracture fragments may be viable, and it is desirable to attempt repair of the humeral head. However, in order to make use of the above-discussed shoulder prostheses of Dine and Dale, the humeral head must be removed and replaced by the prosthetic humeral head which is inserted in the glenoid or shoulder socket. Thus, there is no provision for attempting repair of the humeral head.

Accordingly, it has been desired to manufacture a modular prosthesis which not only is effective for total shoulder joint replacement, but also allows for repair of humeral shaft fractures. That is, the device should allow for both separate or simultaneous treatment of humeral shaft and humeral head fractures. Such a prosthesis should allow for retention of the natural humeral head when it is used for treating humeral shaft fractures in situations where the head is healthy. The prosthesis should offer the surgeon the flexibility to attempt to repair of the fractured humeral head, while allowing a hemi or total arthroplasty to be performed at a later time should the repair prove unsuccessful. Further, the prosthesis should be effective in treating mid-shaft humeral fractures, with the prosthesis constructed so as to span the fracture in patients having longer or tapered bones, with a good fit within the intramedullary cavity of the humeral shaft.

SUMMARY OF THE INVENTION

The present invention is directed to a modular humeral prosthesis for implantation into a humerus of a patient. The invention can be used (1) for shaft fractures, (2) for humeral head fractures, (3) when both shaft and humeral head fractures have occurred, (4) for hemiarthroplasties, and (5) for total arthroplasties. In head fracture cases, either the natural head can be replaced by a prosthesis, or, if the fracture pieces are viable, they can be reconstructed on a fracture cap. Typically the head will be replaced, but the invention gives the surgeon another option. Later, if necessary, the fracture cap can be removed and replaced by a prosthesis head.

The prosthesis includes a proximal humeral component including a distal stem section and a platform disposed on an upper end of the distal stem section. The platform is disposed at an angle to the distal stem section. A tapered projection is disposed on the platform. The prosthesis includes a fracture cap having a peripheral wall and an end wall defining a tapered opening within the fracture cap. The opening has generally the same shape as the tapered projection. The fracture cap is removably disposable on the proximal humeral component by fitting the projection within the opening to create a frictional taper lock. The prosthesis allows the natural humeral head to be reconstructed by reassembling the bone fragments of the natural humeral head about the fracture cap, and securing the reassembled bone fragments to the fracture cap.

In a further embodiment the prosthesis includes a humeral head having a tapered opening therein which has generally the same shape as the tapered projection. The humeral head may be removably disposed on the tapered projection to replace the patient's natural humeral head. The prosthetic humeral head is interchangeable with the fracture cap.

In a further embodiment the invention is directed to a modular humeral prosthesis for implantation into a humerus of a patient, including a proximal humeral component having an upper end and a lower end. The prosthesis also includes a distal stem extension having an upper end and a lower end. The extension is disposed at the lower end of the proximal humeral component.

In a further embodiment the prosthesis includes a locking mechanism which locks the stem extension to the proximal humeral component.

In a further embodiment the invention is directed to a method of implanting a modular humeral prosthesis into a patient to repair a humeral head fracture. The prosthesis includes a proximal humeral component and a fracture cap. The bone fragments of the humeral head are assembled and secured onto the fracture cap. The fracture cap is disposed on the proximal humeral component. The prosthesis is fitted into the patient by insertion of the humeral component into the patient's humeral shaft, with the reconstructed humeral head fitting within the patient's glenoid.

DETAILED DESCRIPTION OF THE PREFERRED EMBODIMENTS

Figure 1:
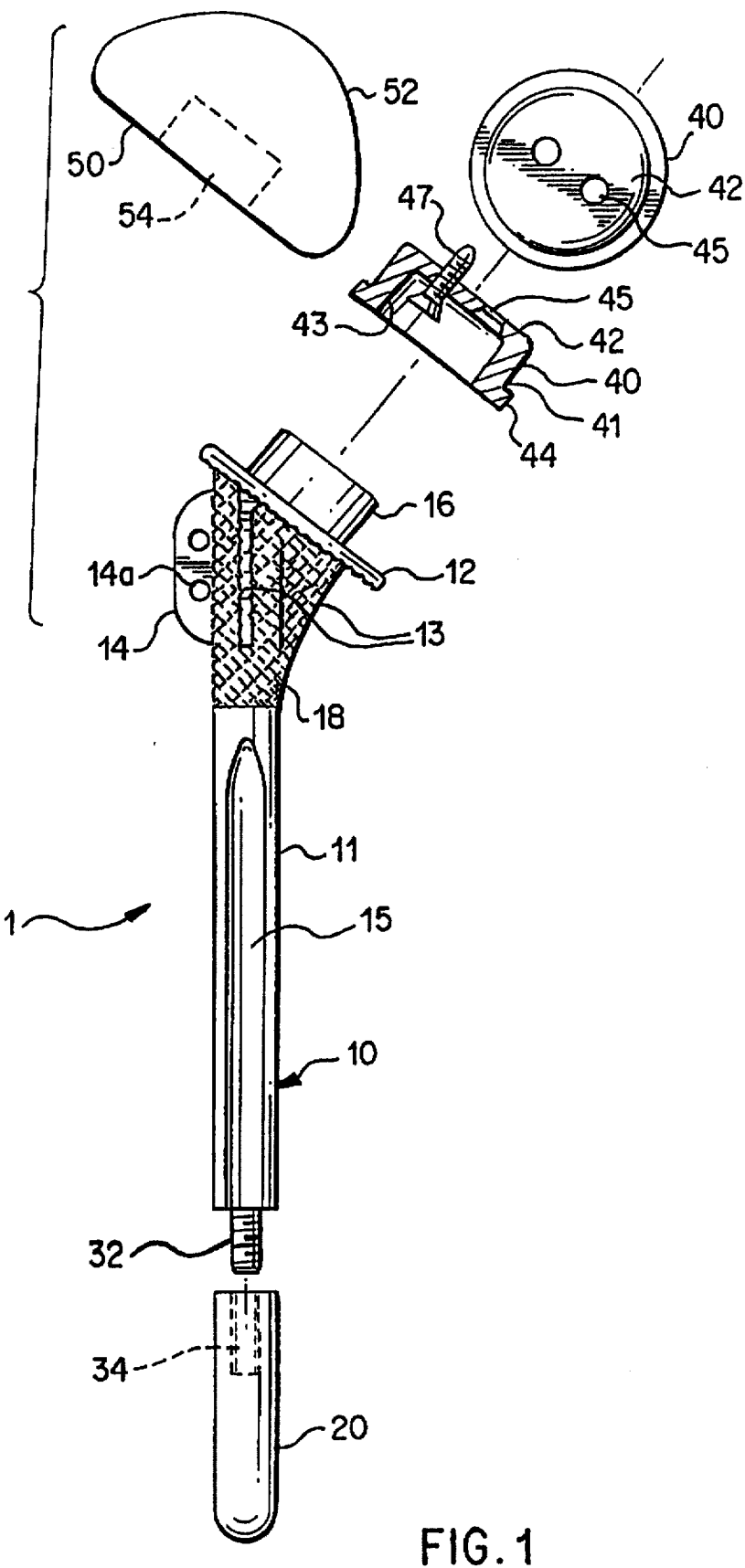
FIG. 1 is a side plan view of a modular humeral prosthesis for fracture and joint replacements according to the invention including a proximal humeral component, a fracture cap, a distal stem extension and a locking mechanism which locks the distal stem extension to the proximal humeral component.

With reference to FIG. 1 a modular humeral prosthesis according to the invention is shown. Prosthesis 1 is shown in a disassembled state and includes proximal humeral component 10, distal stem extension 20, fracture cap 40 and humeral head 50. When assembled, stem extension 20 would be secured and locked upon proximal humeral component 10 in a manner discussed further below. Fracture cap 40 and humeral head 50 are interchangeable, and both are removably disposable upon the upper end of proximal humeral component 10. In use, one of fracture cap 40 or humeral head 50 would be disposed on proximal humeral component 10. Stem extension 20, fracture cap 40 and humeral head 50 are all modular, that is, they are manufactured in different sizes but have a uniform shape and size with respect to the end of proximal humeral component 10 to which they are secured such that any stem extension 20, fracture cap 40 or humeral head 50 may be disposed upon proximal humeral component 10.

Proximal humeral component 10 includes longitudinally extending cylindrical distal stem section 11 having platform 12 disposed on the upper or proximal end thereof. Platform 12 preferably is disposed at an angle of between 30°–α° with respect to the longitudinal axis of cylindrical distal stem section 11. This angle generally is equal to the angle between the axis of the humeral head and the humeral intramedullary canal, that is, the hollow interior of the proximal humerus or humeral shaft. When prosthesis 1 is implanted in a patient, platform 12 acts to prevent subsidence of the implant in the intramedullary canal, and to distribute anatomical loads on the proximal humerus. Tapered cylinder 16 extends upwardly from and is centered with respect to the upper surface of platform 12. Preferably, cylinder 16 has a height of 8 mm and an average diameter of 19 mm. The outer peripheral surface of cylinder 16 tapers radially outwardly in the distal or downward direction at an angle of approximately 2.5°.

Anterior, posterior and medial struts 13 extend outwardly from the proximal or upper end of stem section 11 and serve to provide support for platform 12. Lateral fin 14 also extends outwardly from the upper end of stem section 11. Struts 13 and fin 14 may incorporate suture holes extending therethrough, for example, holes 14a disposed through fin 14. The suture holes may be used to pass sutures therethrough when attaching bone or soft tissue. Stem section 11 also may include longitudinally extending flutes or cement grooves 15 which allow for stem fixation in the humeral canal. Distal stem section 11 of proximal humeral component 10, with the exception of the upper surface of platform 12 and tapered cylinder 16, may be porous coated to allow for bone ingrowth. Such a coating 18 is shown in FIG. 1 at the upper end of distal stem section 11. Distal stem section 11 may have a length range of 33–125 mm measured from the uppermost portion thereof below the lower surface of platform 12, and a diameter range of 6.3–19.1 mm. At the lower end, distal stem section 11 includes cylindrical extension or projection 32 which is externally threaded. Projection 32 preferably is about 13 mm long, has a diameter of 8 mm, and is formed on stem section 11 by cutting or rolling. A small cylindrical polyethylene plug (not shown) may be press fit into a hole formed in the externally threaded projection.

Prosthesis 1 also includes distal stem extension 20. Stem extension 20 may be rounded at its lower end and is formed with recess 34 in the upper end. Recess 34 is internally screw-threaded, for example, by use of a standard or spiralock internal thread. Both are formed by either cutting or rolling.

The threaded portion of threaded recess 34 is generally the same length and diameter as threaded projection 32 and is threaded with a corresponding pitch. Threaded recess 34 and threaded projection 32 jointly form a locking mechanism which allows stem extension 20 to be secured and locked to proximal humeral component 10 by screwing projection 32 in recess 34. The polyethylene plug incorporated into the thread form of projection 32 acts to create an interference fit between stem extension 20 and proximal humeral component 10.

Stem extension 20 is manufactured in a variety of sizes having different lengths and, if desired, different diameters. However, the shape and dimensions of recess 34 are uniform for all stem extensions. Thus, stem extension 20 is modular, and any stem extension 20 may be secured to proximal humeral component 10. For example, the manufacture of stem extensions having different lengths but with a uniform locking component is shown with respect to the variations in the locking mechanisms shown in FIGS. 2 and 8, and this modularity aspect of the prosthesis is incorporated into the invention for each variation of the locking mechanism. In addition, proximal humeral component 10 could be manufactured with different sizes, for example, with distal stem sections 11 of differing lengths.

Figure 8:
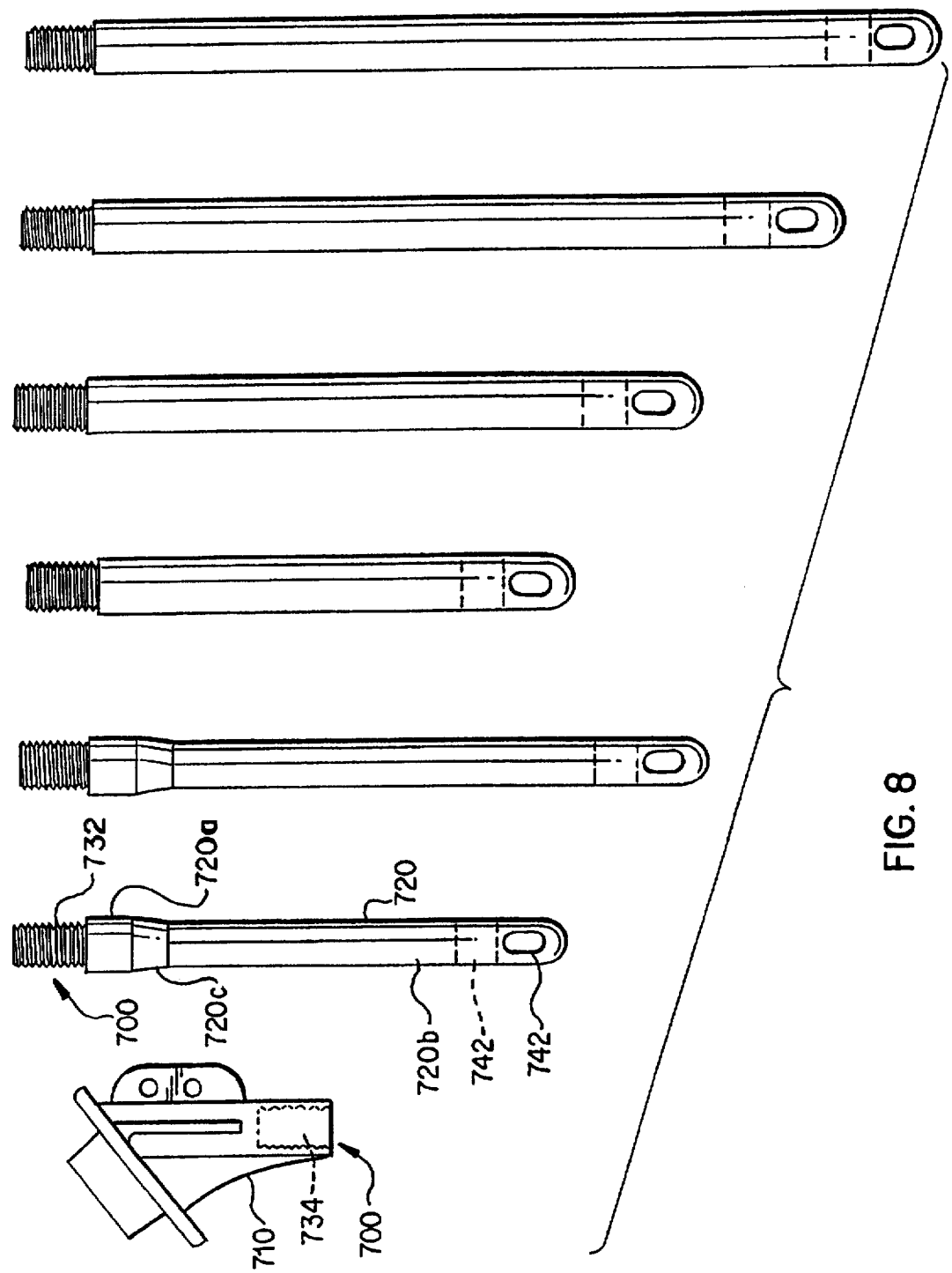

Accordingly, by selecting a stem extension 20 of appropriate dimensions, and securing it to a selected proximal humeral component 10 by the locking mechanism, prosthesis 1 can be custom fitted to an individual patient. For example, for patient's with relatively long humeral shafts and having a mid-shaft fracture, a longer stem extension 20 would be selected so as to allow the prosthesis to extend beyond the fracture point. For patient's having an excessively tapered humeral shaft, stem extension 20 would be tapered to allow the prosthesis to extend past the fracture while maintaining a good fit within the intramedullary canal. An example of tapering is shown in FIG. 8.

Prosthesis 1 also includes fracture cap 40 which allows for reconstruction of the natural humeral head by allowing the fragments of the head to be secured to the cap and then inserted within the glenoid. Fracture cap 40 is cup-shaped, having generally cylindrically-shaped outer peripheral wall 41 and end wall 42 defining tapered opening 43. Screw holes 45 are disposed through end wall 42. Securing screws 47 may be disposed through screw holes 45 from the interior side and screwed into the bone fragments to secure them to the fracture cap. Flange portion 44 extends about the periphery of outer peripheral wall 41. Tapered opening 43 has generally the same shape and dimensions as tapered cylinder 16 of proximal humeral component 10. Fracture cap 40 may be disposed and secured on proximal humeral component 10 by fitting tapered cylinder 16 within tapered opening 43, so as to provide a frictional taper lock, with flange portion 44 resting parallel to the upper surface of platform 12. The frictional taper lock is strong enough to secure and lock fracture cap 40 on proximal humeral component 10 so as to effectively preclude fracture cap 40 from being removed from proximal humeral component 10 due to the ordinary forces encountered while implanted in a patient. However, fracture cap 40 may be removed from proximal humeral component 10 by application of a substantial longitudinal force, even while distal stem section 11 is disposed in the humeral shaft. Fracture cap 40 is disposed on tapered cylinder 16 with a clearance maintained between flange portion 44 and the upper surface of platform 12 to ensure the taper locks prior to contact between the two parts.

As with distal stem extension 20, fracture cap 40 is modular with respect to proximal humeral component. Fracture cap 40 may be manufactured in different sizes, for example, so as to have different overall diameters or lengths, but with the dimensions of the tapered opening being uniform. Thus, any fracture cap 40 may be secured and locked on proximal humeral component 10. The lengths of the fracture cap range between 8 mm and 16 mm, and the diameters range between 22 mm and 35 mm.

Figure 1A:
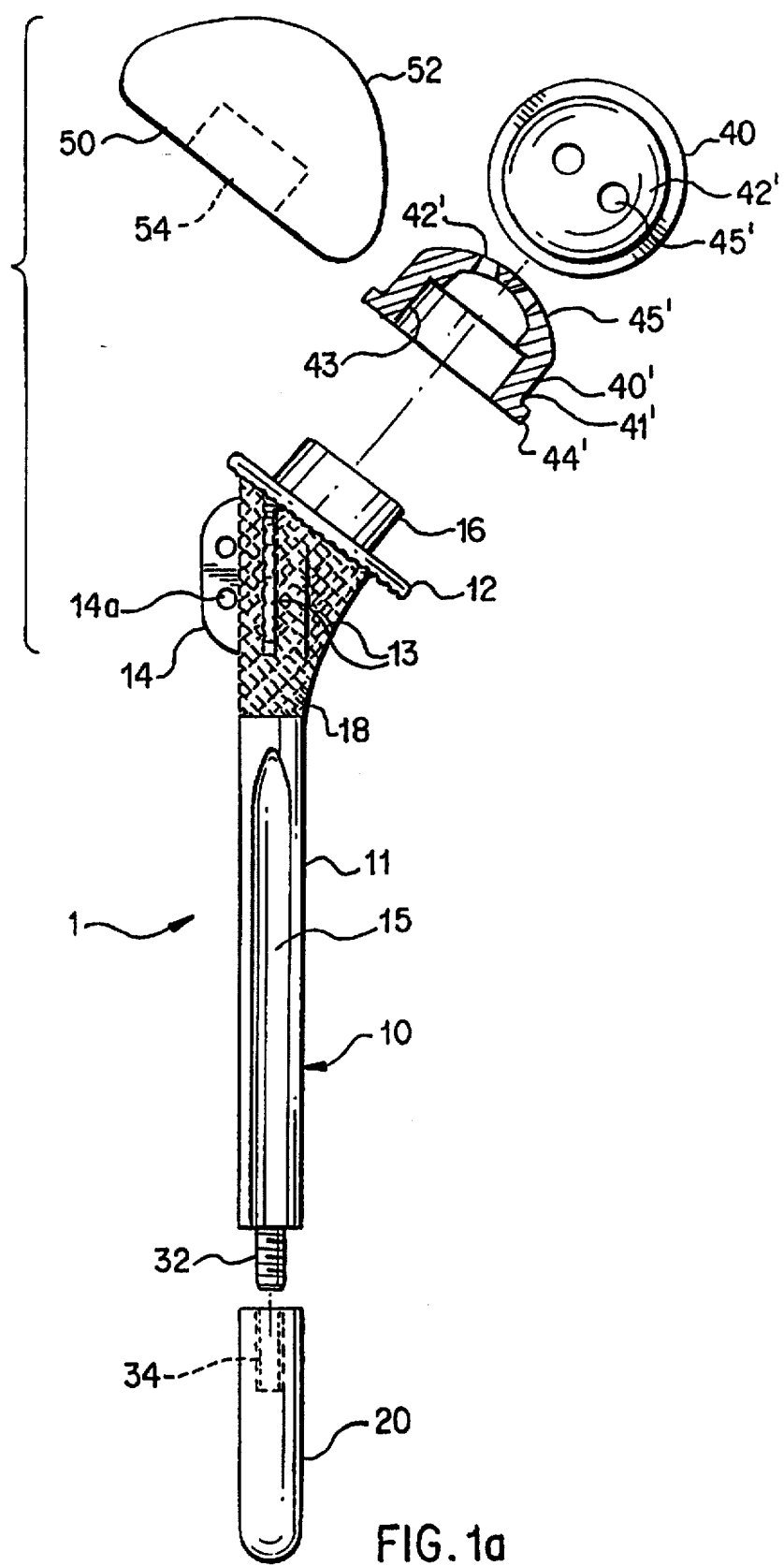
FIG. 1a shows a modular humeral prosthesis including a variation of the fracture cap shown in FIG. 1.

End wall 42 of fracture cap 40 may be flat as shown in FIG. 1. Alternatively, as shown in FIG. 1a, fracture cap 40' may include end wall 42' which is dome shaped and which contains screw holes 45' disposed at various angles. In both embodiments, fracture cap 40,40' is shaped and sized such that after implantation of prosthesis 1 into the patient, a space is maintained between the fracture cap and the glenoid. The space is generally the same size as the patient's natural humeral head, and as explained further below, is sufficient to allow the bone fragments of the humeral head, which are reassembled about and secured upon the fracture cap by screws 47, to fit within the glenoid. Thus, fracture cap 40 is useful in reconstructing the patient's natural humeral head.

Prosthesis 1 also includes-humeral head 50 having an essentially hemispherical shape. Head 50 includes upper spherical articulation surface 52 which is shaped to fit directly within the glenoid, or alternatively, within a matching glenoid prosthesis. Surface 52 is preferably highly polished. The spherical radius of surface 52 is designed to match anatomical humeral dimensions or to satisfy a predetermined relationship with a glenoid prosthesis. Humeral head 50 is used when it is necessary to replace the patient's natural humeral head, for example, when the head is badly damaged. Though prosthesis 1 includes both humeral head 50 and fracture cap 40, these components are interchangeable and only one would be used in assembling a prosthesis for implantation into a patient.

Humeral head 50 also includes tapered opening 54 which corresponds in shape and dimension with tapered cylinder 16, to thereby provide a taper lock as described above with respect to fracture cap 40. The taper lock secures and locks humeral head 50 on proximal humeral component 10 so as to effectively preclude it from being removed due to the ordinary forces encountered while implanted in a patient. However, head 50 may be removed from proximal humeral component 10 by application of a substantial longitudinal force, even while distal stem section 11 is disposed in the humeral shaft.

As with fracture cap 40, humeral head 50 is modular, that is, it is manufactured in different sizes but with a uniformly sized tapered opening 54 which allows any humeral head 50 to be removable disposed on proximal humeral component 10. Humeral heads 50 are manufactured to have spherical radii ranging from 19 mm to 32 mm and diameters ranging from 36 mm to 64 mm.

Figure 2:
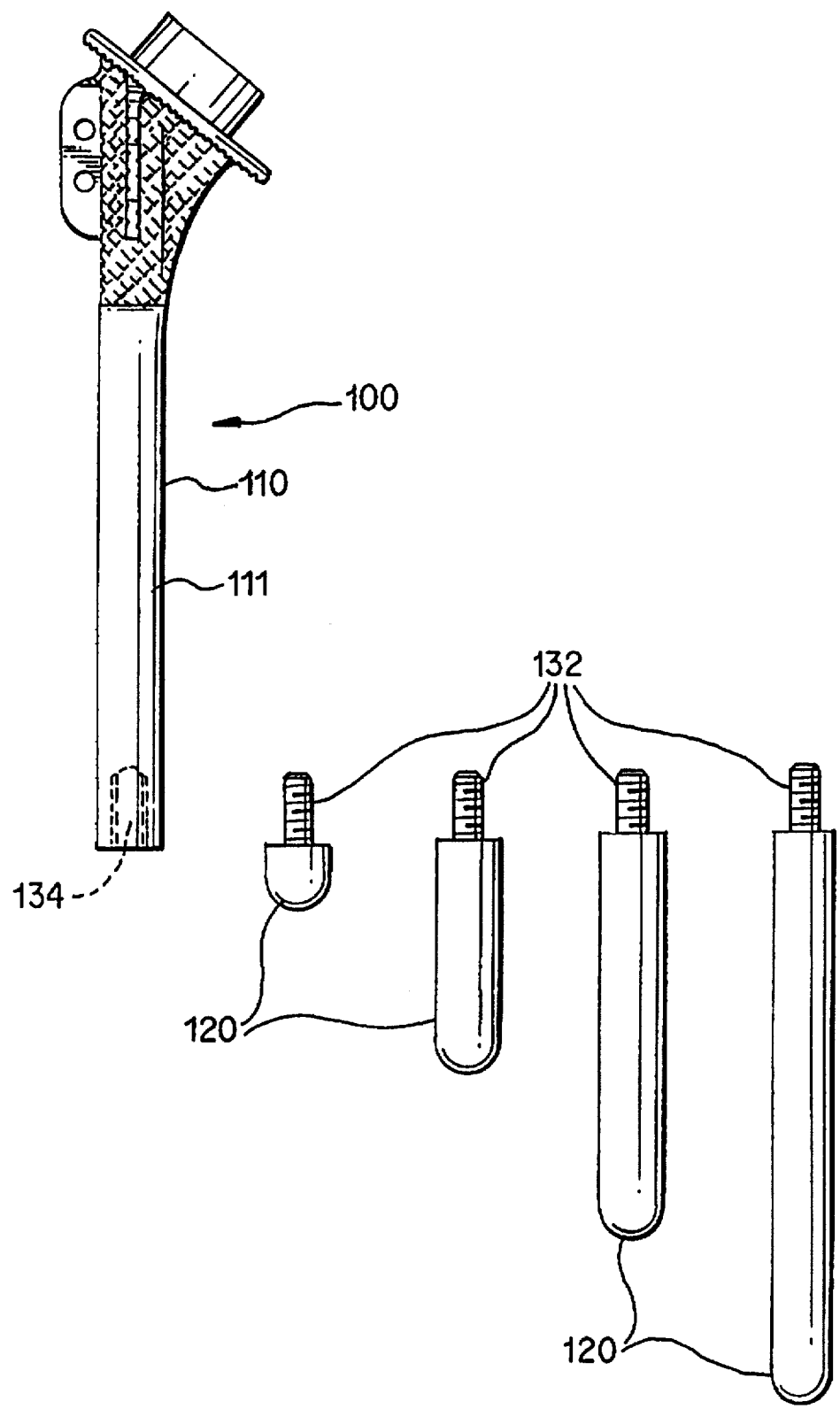
FIGS. 2-8 are side plan views showing alternative variations of the locking mechanism.

With reference to FIG. 2, a modular humeral prosthesis including an alternative configuration of the locking mechanism shown in FIG. 1 is disclosed. Prosthesis 100 includes proximal humeral component 110 having cylindrical distal stem section 111. Though not shown, distal stem section 111 could include flutes such as flutes 15 shown in FIG. 1. Internally threaded recess 134 having a structure similar to recess 34 in FIG. 1 is formed on the lower end of stem section 111. Distal stem extension 120 includes externally threaded extension or projection 132 having a structure similar to projection 32 in FIG. 1. Extension 132 and recess 134 jointly form a locking mechanism which serves to secure and lock distal stem extension 120 to stem section 111 in the same manner as discussed above with respect to FIG. 1. Further, a plurality of stem extensions 120 having different lengths but uniformly sized extensions 132 is shown in FIG. 2, and is evident of the modular aspect of the invention. The lengths of extensions 120 range from 6 mm to 216 mm.

With reference to FIGS. 3-8, prostheses according to the invention and including variations of the locking mechanism which locks the distal stem extension to the proximal humeral component are disclosed. The variations in the locking mechanism include corresponding differences in the structures of the distal stem section of the proximal humeral component and the distal stem extension. Only those portions of the proximal humeral component and the distal stem extension which are different in each embodiment will be discussed, with those portions having substantially the same structure also having the same numbering as in FIGS. 1 and 2. Further, though not shown, the structures of the fracture cap and humeral head would be the same for each figure.

Figure 3:
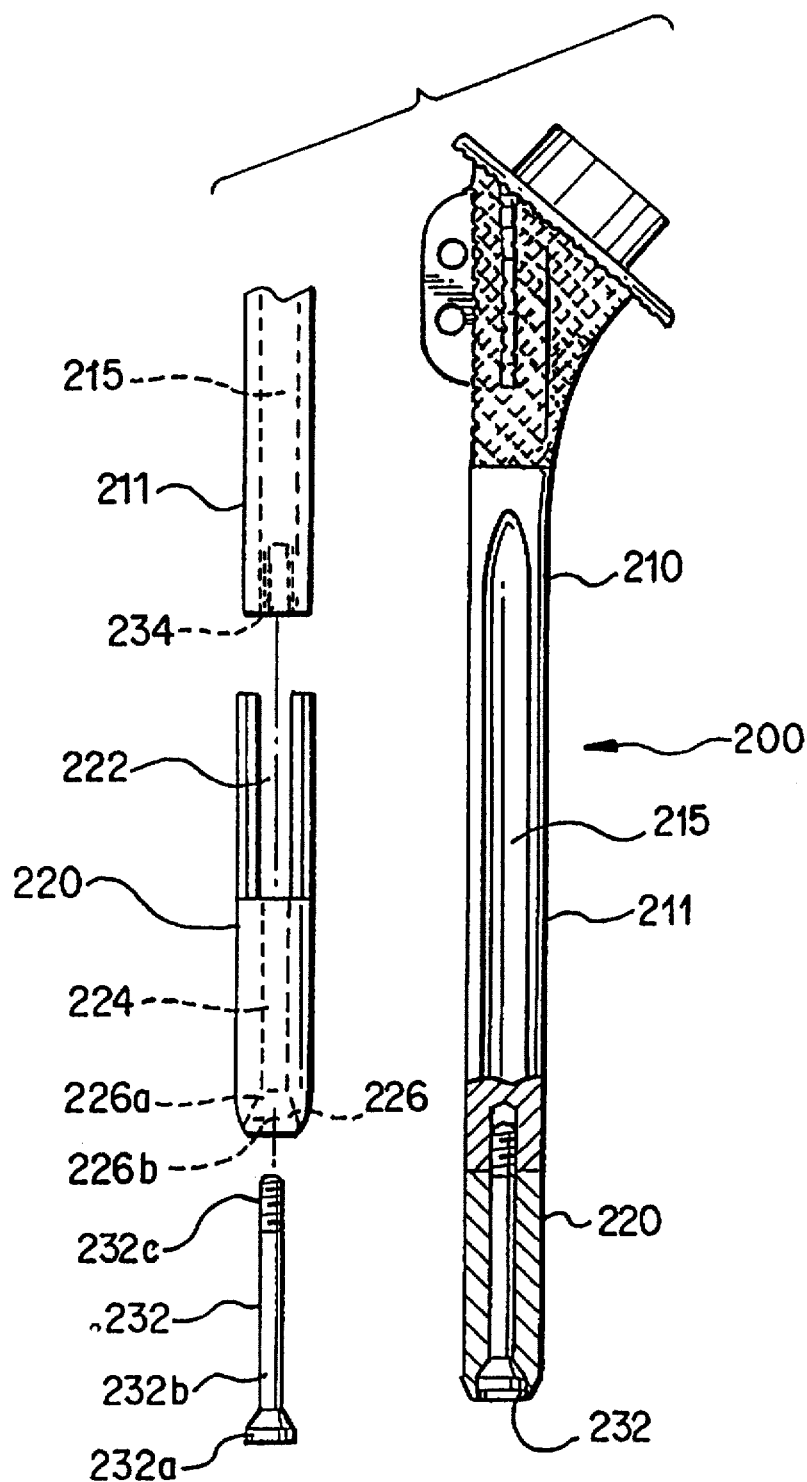

With reference to FIG. 3, a modular humeral prosthesis including a variation in the locking mechanism is shown. Prosthesis 200 includes proximal humeral component 210 having cylindrical stem section 211 with flutes 215. Stem section 211 includes internally screw-threaded recess 234 formed in the lower end thereof. Recess 234 could be formed in the same manner as recess 34 in FIG. 1.

Distal stem extension 220 includes stem section opening 222 formed therein and extending downwardly from the proximal end. Stem section opening 222 has a diameter which is approximately equal to the diameter of distal stem section 211, for example, 9.5 mm. Distal stem extension 220 also includes screw opening 224 formed therein and extending downwardly from the lower end of opening 222 to the lower end of stem extension 220. Screw opening 224 has a smaller diameter than stem section opening 222, for example, 6 mm, and may have a length of 20 mm. At the lower end, the diameter of screw opening 224 increases to form head opening 226 having upper conical portion 226a and lower cylindrical portion 226b. The average diameter of upper portion 226a may be 7 mm and the diameter of lower portion 226b may be 8 mm.

Locking screw 232 includes head 232a, cylindrical extending portion 232b and screw-threaded portion 232c. Head 232a has approximately the same shape and dimensions as head opening 226. Cylindrical extending portion 232b has approximately the same length and diameter as screw opening 224. The length and diameter of screw-threaded portion 232c is approximately equal to the length of recess 234, and portion 232c has a corresponding thread pitch. Accordingly, the overall length of locking screw 232 is generally equal to the overall length of head opening 226, screw opening 224 and recess 234.

Distal stem extension 220 may be secured and locked upon proximal humeral component 210 by insertion of cylindrical stem section 211 into stem section opening 222. The lower end of stem section 211 rests upon the upper inner surface of stem extension at the location of the upper end of screw opening 224. Locking screw 232 is disposed through screw opening 224 and is screwed into screw-threaded recess 234 to secure and lock distal stem extension 220 on proximal humeral component 210, with head 232a resting in head opening 226. Distal stem extension 220 is modular, and is manufactured so that the diameter of opening 222 and length and diameter of opening 224 are uniform. The overall length of distal stem extension 220 may be varied by varying the length of opening 222. Alternatively, the length of distal stem extension 220 may be varied by varying the length of screw opening 224, with a corresponding variation in the length of cylindrical extending portion 232b of locking screw 232. The size of head 232a and screw-threaded portion 232c would be uniform.

Figure 4:
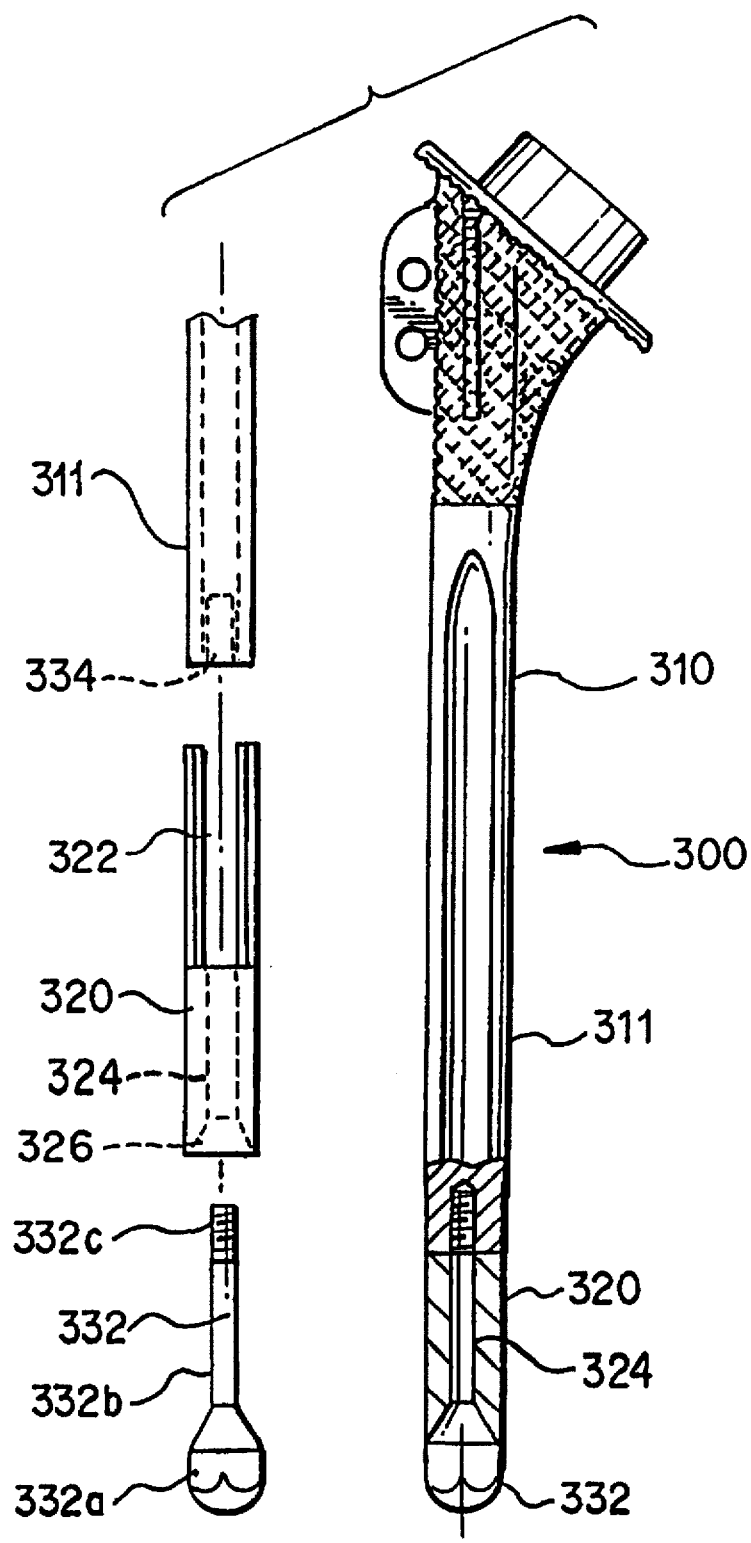

With reference to FIG. 4, an alternative configuration of the locking mechanism of FIG. 3 is shown. Prosthesis 300 is substantially identical with prosthesis 200 of the third embodiment, and includes proximal humeral component 310 including cylindrical stem section 311 and threaded recess 334. Distal stem extension 320 includes distal stem opening 322 and screw opening 324. However, head opening 326 of screw opening 324 has a conical shape extending to the bottom of distal stem extension 320. Locking screw 332 includes screw head 332a, cylindrical extending portion 332b and screw-threaded portion 332c. Screw head 332a includes both a conical portion corresponding in shape and size with head opening 326 and a multi-sided head portion.

Distal stem extension 320 is secured and locked to stem section 311 by locking screw 332 in the same manner as discussed with respect to the variation shown in FIG. 3. The conical portion of screw head 332a fits within head opening 326, with the multi-sided portion of screw head 332a disposed exteriorly of distal stem extension 320. This configuration provides the further advantage of a uniform tip.

Figure 5:
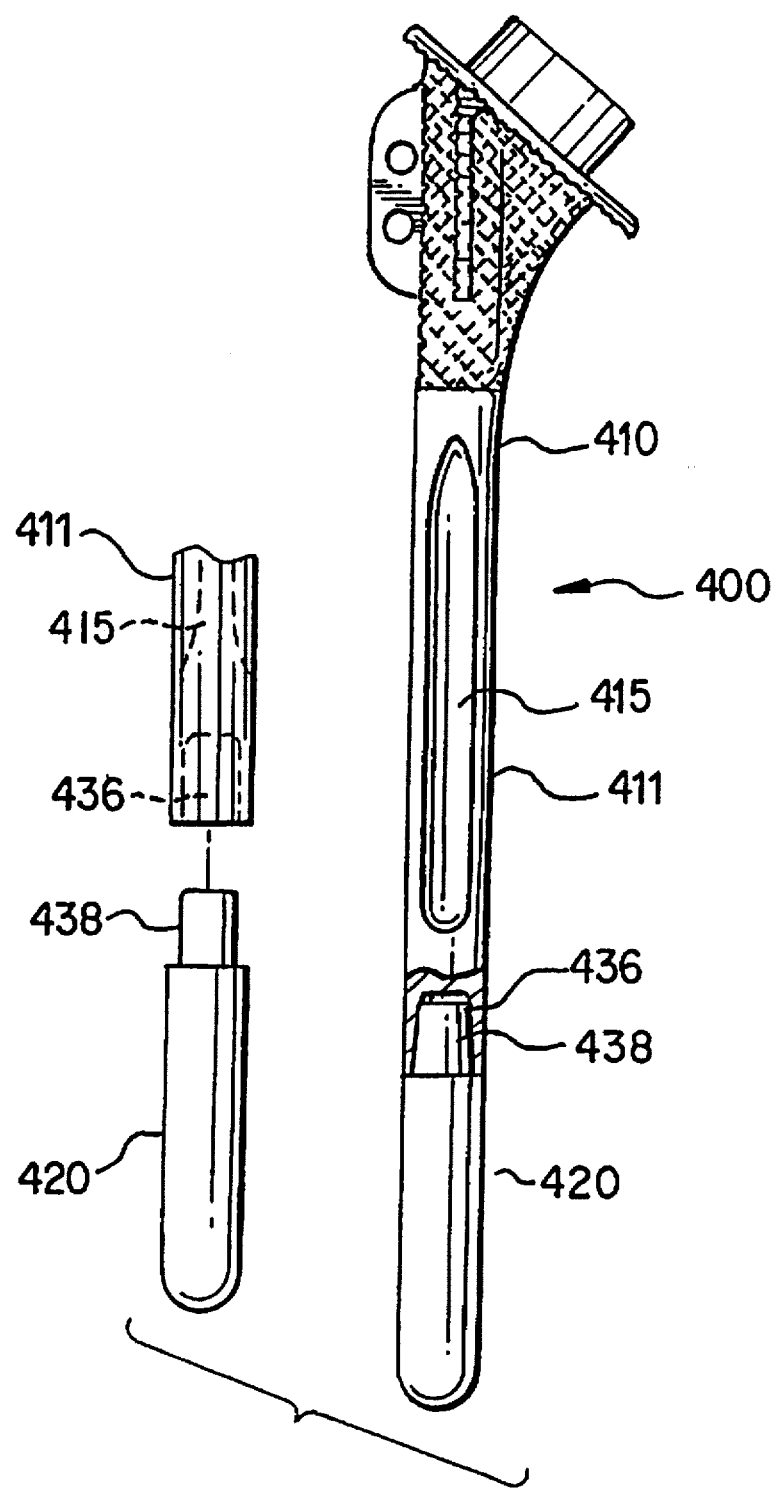

With reference to FIG. 5, a modular humeral prosthesis including a further variation in the locking mechanism is shown. Prosthesis 400 includes proximal humeral component 410 having cylindrical distal stem section 411 including longitudinal flutes 415 formed on the exterior surface. Tapered recess 436 is formed in the lower end of stem section 411. Recess 436 may have a length of 13 mm, an upper diameter of 8.4 mm and a lower diameter of 9.5 mm.

Modular distal stem extension 420 includes tapered projection 438 extending from the upper end thereof. Tapered projection 438 corresponds in shape to tapered recess 436. Distal stem extension 420 may be secured and locked to proximal humeral component 410 by insertion of projection 438 within recess 436, thereby providing a taper lock which secures the components together by a frictional fit. The frictional taper lock is strong enough to secure and lock distal stem extension 420 on proximal humeral component 410 so as to effectively preclude unintentional removal due to the ordinary forces encountered while implanted in a patient. However, stem extension 420 may be removed from proximal humeral component 410 by application of a substantial longitudinal force.

Figure 6:
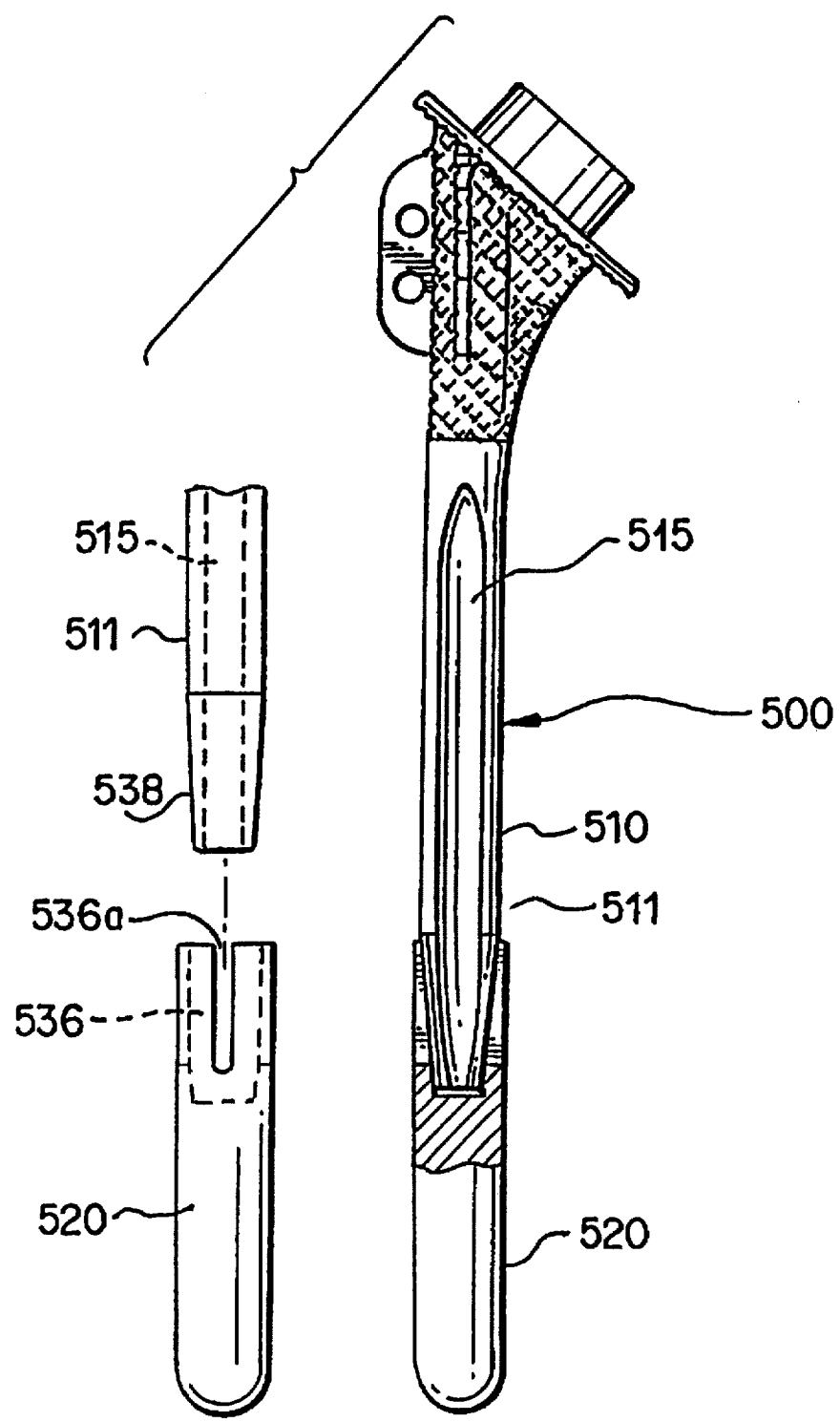

With reference to FIG. 6, an alternative configuration of the locking mechanism of FIG. 5 is shown. Prosthesis 500 includes proximal humeral component 510 having cylindrical distal stem section 511 including longitudinal flutes 515. Stem section 511 includes tapered lower end or projection 538 which may have a length of 13 mm, an upper diameter of 9.5 mm and a lower diameter of 8.4 mm. Modular distal stem extension 520 includes tapered recess 536 corresponding in shape and dimensions to tapered distal end 538. Recess 536 includes longitudinal slit 536a extending from the upper end and terminating above the lower inner surface of recess 536. Distal stem extension 520 may be secured and locked to proximal humeral component 510 by insertion of tapered distal end 538 within tapered recess 536, thereby providing a taper lock which secures the components together by a frictional fit. Longitudinal slit 536a allows the tapered recess to open slightly when the tapered distal end 538 is impacted into place.

Figure 7:
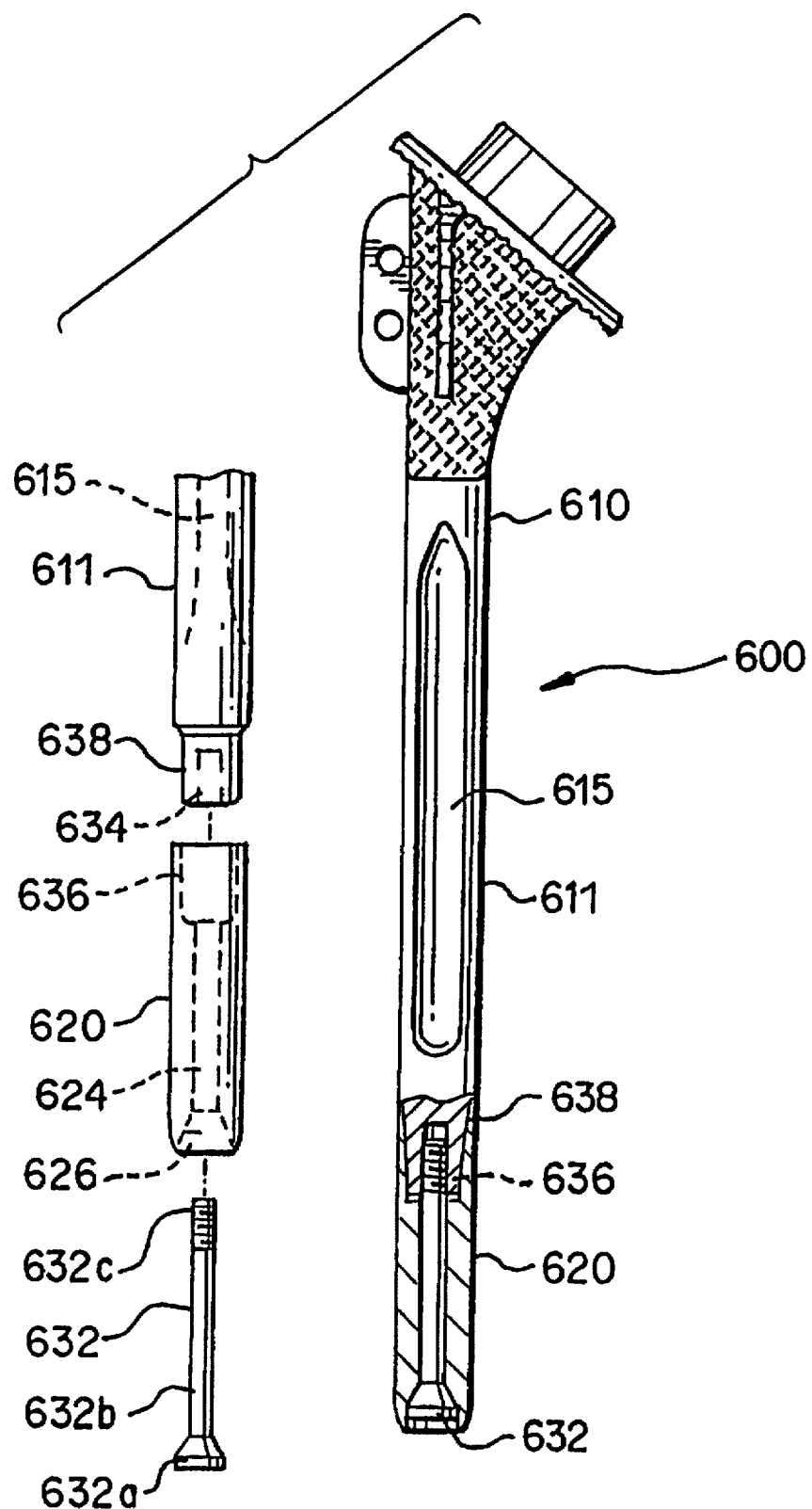

With reference to FIG. 7, a modular humeral prosthesis including a combination of the locking mechanisms shown in FIGS. 3 and 5 is shown. Prosthesis 600 includes proximal humeral component 610 having cylindrical distal stem section 611 including longitudinal flutes 615. Stem section 611 includes tapered projection 638 at the lower end and having a structure similar to projection 438 shown in FIG. 5. Projection 638 includes threaded recess 634 having a structure similar to recess 234 in FIG. 3. Modular distal stem extension 620 includes tapered recess 636 having a structure similar to that of recess 436 shown in FIG. 5 and corresponding in shape and dimension to tapered projection 638. Distal stem extension 620 also includes longitudinal screw opening 624 extending downwardly from tapered recess 636 and head opening 626 extending downwardly from opening 624. Screw opening 624 and head opening 626 have a structure similar to that of screw opening 224 and head opening 226 shown in FIG. 3.

Locking screw 632 is similar in structure to locking screw 232 shown in FIG. 3 and includes screw head 632a, cylindrical extending portion 632b and screw-threaded portion 632c. Screw head 632a has approximately the same shape and dimensions as head opening 626, and cylindrical extending portion 632b has approximately the same length and diameter as screw opening 624. The shape and dimensions of screw-threaded portion 632c are approximately equal to the shape and dimension of threaded recess 634, and portion 632c has a corresponding thread pitch. Accordingly, the overall length of locking screw 632 is generally equal to the overall length of head opening 626, screw opening 624 and threaded recess 634.

Distal stem extension 620 may be secured and locked to proximal humeral component 610 by insertion of tapered projection 638 within tapered recess 636, thereby providing a taper-lock which secures and locks the components together by a frictional fit, in the same manner as the taper lock shown in FIG. 5. Further locking screw 632 is inserted through screw hole 624 and is screwed into screw-threaded recess 634 to further secure and lock distal stem extension 620 on proximal humeral component 610, with head 632a resting in head opening 626. Prosthesis 600 thus provides two ways to secure the distal stem extension to the proximal humeral component.

With reference to FIG. 8, a modular humeral prosthesis including a further variation in the locking mechanism is shown. Prosthesis 700 includes proximal humeral component 710 having screw-threaded recess 734 formed therein. Prosthesis 700 further includes modular distal stem extension 720 having corresponding screw-threaded projection 732 extending from the upper end. Projection 732 may be screwed into threaded recess 734 to secure and lock stem extension 720 to proximal humeral component 710. Stem extension 720 also includes holes 742 disposed therethrough which allow for use of cross screws to fix the prosthesis within the humerus.

A plurality of stem extensions 720 having different lengths, and in some cases, constructed so as to taper inwardly in the downward direction, are shown in FIG. 8. Extensions 720 which are tapered include first cylindrical portion 720a having a first diameter and forming the upper end of extension 720, a second cylindrical portion 720b having a second diameter which is smaller than the first diameter and forming the lower end of extension 720, and a third, tapered portion 720c disposed between the first and second portions. However, each distal stem extension 720 includes threaded projection 732 having a uniform length and diameter. Accordingly, any distal stem extension 720 may be secured and locked to proximal humeral component 710 by screwing threaded projection 732 into threaded recess 734. The selection of a particular stem extension is based upon the size of the intramedullary canal of the patient's humerus as well as whether the intramedullary canal is tapered inwardly.

Figure 9:
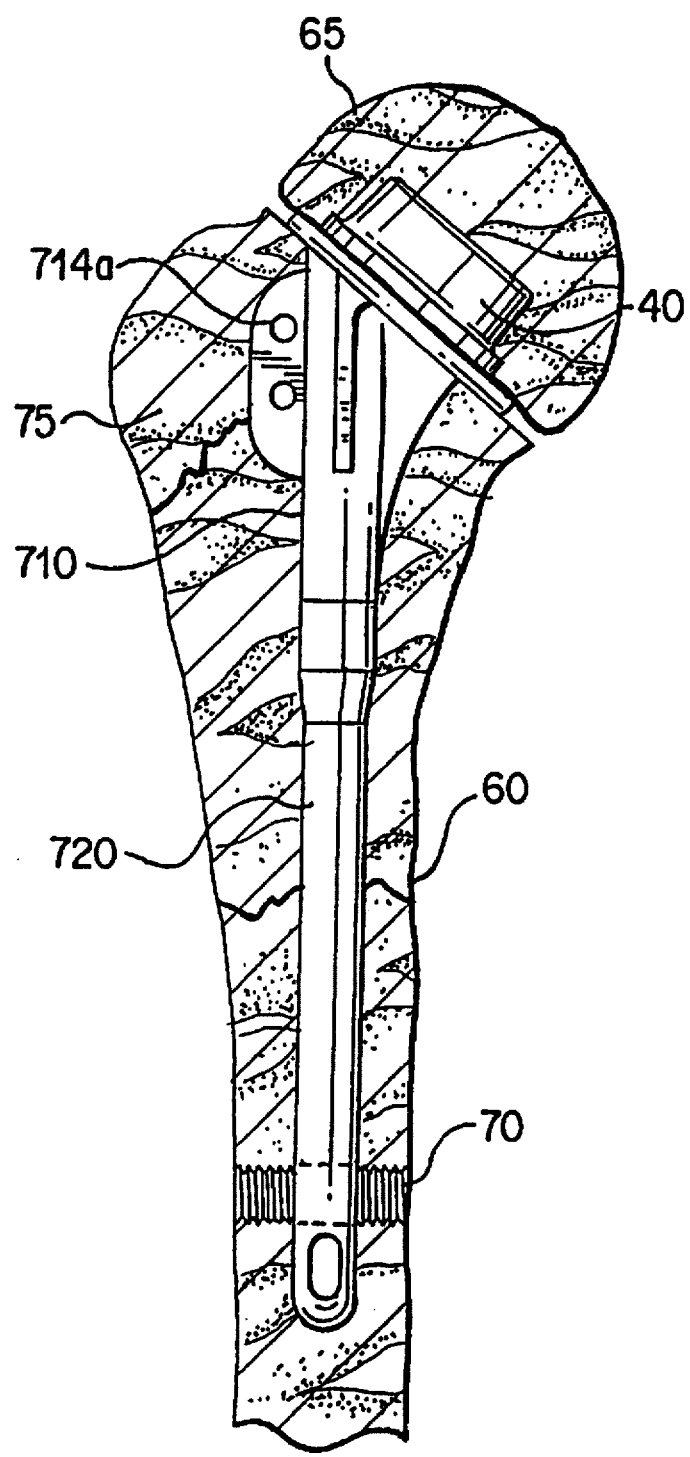
FIG. 9 is a side plan view showing the prosthesis according to the present invention disposed in a human humerus.

With reference to FIG. 9, the use of a prosthesis according to the present invention for repairing a fractured humerus is shown. In particular, FIG. 9 shows a four-part fracture. The four parts of the fracture are: 1) humeral shaft 60 which is the largest fragment, and which is shown as divided again because of a mid-shaft fracture, 2) humeral head fragment 65, which is placed on fracture cap 40, 3) greater tuberosity fragment 75, and 4) the lesser tuberosity fragment (not shown). In the situation shown, the fracture is repaired by prosthesis 700 of FIG. 8, although any of the prostheses shown in FIGS. 1–8 could be used. Distal stem extension 720 is selected based upon the length of the patient's humeral shaft and whether the intramedullary canal is tapered so as to make the use of a tapered stem extension desirable. The selected distal stem extension is secured and locked to the proximal humeral component. If desired, different-sized stem extensions 720 may be tried by insertion in and removal from the humeral shaft until a stem extension having an appropriate size and taper is found. Fracture cap 40 having a size which is appropriate for the patient is chosen.

The bone fragments of humeral head 65 are reassembled about fracture cap 40 and may be secured thereto by inserting securing screws 47 (not shown in FIG. 9) through the screw holes and into the bone fragments. Thus, the natural humeral head is reconstructed about fracture cap 40. The reconstructed humeral head and fracture cap are then secured upon proximal humeral component 710 via the taper lock discussed above. Prosthesis 700 is inserted within humeral shaft 60, and is secured thereto by cross screws 70 if necessary. Fracture fragments are secured to prosthesis 700 through suture holes 714a. The reconstructed natural humeral head is then inserted in the patient's glenoid to complete implantation. If necessary, a separate glenoid prosthesis may be used.

Alternatively, if the natural humeral head is healthy, a fracture cap may be inserted therein after proximal humeral component 710 and stem extension 720 are inserted in humeral shaft 60.

If the fracture of the humeral head is severe enough so as to preclude reconstruction, the humeral head is not viable, or in arthritis cases where cartilage is degenerated humeral head 50 of an appropriate size would be used in place of fracture cap 40. Humeral head 50 would be inserted in the glenoid or glenoid prosthetic. Furthermore, should the use of fracture cap 40 to reconstruct the humeral head prove unsuccessful, fracture cap 40 and the reconstructed bones can be removed and replaced by humeral head 50.

The prosthesis according to the above-described invention thus allows for repair of humeral shafts of many different sizes and shapes, as well as reconstruction of the humeral head. If reconstruction of the humeral head ultimately proves unsuccessful, the invention allows for subsequent replacement of the reconstructed humeral head by an artificial humeral head. If it is determined initially that the humeral head is damaged so severely as to preclude reconstruction, the prosthesis can be assembled with a prosthetic humeral head.

All parts of the prosthesis according to the present invention may be manufactured from known implantable grade material, for example, Ti6A14V or CoCrMo. The proximal humeral components and humeral heads may be cast, while the stem extension may be cast or machined from wrought bar stock. The humeral heads also may be made of a ceramic material such as alumina or zirconia.

We claim:

1. A modular humeral prosthesis for implantation into a humerus of a patient, the humerus including a natural humeral shaft and a natural humeral head, said prosthesis comprising:

a proximal humeral component including a distal stem section and a platform disposed on an upper end of said distal stem section, said platform disposed at an angle to said distal stem section, said proximal humeral component including a tapered projection disposed on said platform;

a fracture cap, said fracture cap having a peripheral wall and an end wall defining a tapered opening within said fracture cap, said tapered opening having generally the same shape as said tapered projection, said fracture cap removably disposed on said proximal humeral component by fitting said projection within said opening to create a frictional taper lock; and a bone structure attachable to said fracture cap serving to fixedly secure reassembled bone fragments of the natural humeral head to said fracture cap to reconstruct the natural humeral head.

2. The prosthesis recited in clam 1, said end wall of said fracture cap having a plurality of screw holes disposed therethrough, said bone securement structure comprising a plurality of securing screws, the reassembled bone fragments being secured to said fracture cap by inserting said securing screws through the screw holes and into the fragments.

3. The prosthesis recited in claim 1 further comprising a distal stem extension, said stem extension joined to a lower end of said distal stem section, wherein, said distal stem section and said stem extension include a modular component so as to allow proximal humeral components and distal stem extensions of different sizes to be joined together.

4. The prosthesis recited in claim 3 further comprising locking means for locking said distal stem extension to said proximal humeral component.

5. The prosthesis recited in claim 4, wherein, said modular component is said locking means.

6. The prosthesis recited in claim 1, wherein, a portion of the exterior surfaces of said prosthesis are porous coated.

7. The prosthesis recited in claim 1, wherein, said end wall is substantially flat and said peripheral wall is generally cylindrically-shaped.

8. The prosthesis recited in claim 1, wherein, said end wall is substantially dome-shaped and said peripheral wall is generally cylindrically-shaped.

9. A method of implanting a modular humeral prosthesis into a patient to repair a humeral head fracture, using a set of modular humeral prosthesis components, said method comprising the steps of:

providing a set of modular humeral prosthesis components, including a fracture cap, a bone securement structure attachable to said fracture cap and serving to fixedly secure reassembled bone fragments of the natural humeral head to said fracture cap to reconstruct the natural humeral head, a prosthesis humeral head and a proximal humeral component;

inspecting said humeral head fracture;

selecting for implantation, based on the severity of said fracture, one of said fracture cap and said prosthetic humeral head; and fitting the prosthesis into the patient by insertion of the proximal humeral component into the patient's humeral shaft and undertaking one of a reconstructing the bone fragments of the patient's natural humeral head by assembling the bone fragments onto the fracture cap, fixedly securing the fragments on the fracture cap with said bone securement structure to reconstruct the natural humeral head, and disposing the fracture cap on the proximal humeral component; and (b) replacing the natural humeral head with said prosthetic humeral head and disposing the prosthetic humeral head on the proximal humeral component.

10. A set of modular components for implantation of a humeral prosthesis into a humerus of a patient, the humerus including a natural humeral shaft and a natural humeral head, said set comprising:

a proximal humeral component including a distal stem section and a platform disposed on an upper end of said distal stem section, said platform disposed at an angle to said distal stem section, said proximal humeral component including a tapered projection disposed on said platform;

a fracture cap, said fracture cap having a peripheral wall and an end wall defining a tapered opening within said fracture cap, said tapered opening having generally the same shape as said tapered projection, said fracture cap removably disposed on said proximal humeral component by fitting said projection within said opening to create a frictional taper lock;

a bone securement structure attacheble to said fracture cap serving to fixedly secure reassembled bone fragments of the natural humeral head to said fracture cap to reconstruct the natural humeral head; and a prosthetic humeral head having a tapered opening, said tapered opening of said prosthetic humeral head having generally the same shape as said tapered projection, said prosthetic humeral head being removably disposable on said proximal humeral component by fitting said projection within said opening of said prosthetic humeral head to create a frictional taper lock, whereby, said prosthetic humeral head is interchangeably disposable, with said fracture cap, on said proximal humeral component.

* * * * *

UNITED STATES PATENT AND TRADEMARK OFFICE
CERTIFICATE OF CORRECTION

PATENT NO. : 5,702,486
DATED : December 30, 1997
INVENTOR(S) : Craig et al.

It is certified that error appears in the above-identified patent and that said Letters Patent is hereby corrected as shown below:

```
Column 1, line 26, change "pans" to --parts--;
    line 29, change "an" to --art--;
    line 43, change "humera" to --humeral--.
Column 3, line 58, change "-d°" to --60°--.
Column 5, line 59, delete "-".
Column 10, line 57, after "bone" insert --securement--.
Column 11, line 29, change "prosthesis" to --prosthetic--;
    line 37, change "a" to --(a)--.
Column 12, line 26, change "attacheble" to --attachable--;
    line 26, after "cap", insert --and--.
```

Signed and Sealed this

Twenty-eighth Day of April, 1998

Attest:

BRUCE LEHMAN

*Attesting Officer*　　　　　*Commissioner of Patents and Trademarks*